(12) United States Patent
Al Wakeel

(10) Patent No.: US 9,132,223 B1
(45) Date of Patent: Sep. 15, 2015

(54) PERITONEAL DIALYSIS CATHETER

(71) Applicant: KING SAUD UNIVERSITY, Riyadh (SA)

(72) Inventor: Jamal Saleh Al Wakeel, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 14/607,928

(22) Filed: Jan. 28, 2015

(51) Int. Cl.
    *A61M 1/28*     (2006.01)
    *A61M 25/00*    (2006.01)
    *A61M 39/10*    (2006.01)

(52) U.S. Cl.
    CPC ............ *A61M 1/285* (2013.01); *A61M 25/002* (2013.01); *A61M 39/1011* (2013.01); *A61M 2039/1033* (2013.01); *A61M 2210/1017* (2013.01)

(58) Field of Classification Search
    CPC ................. A61M 1/28; A61M 39/10; A61M 2039/1033; A61M 2039/1077; A61M 39/20
    USPC ............................................. 604/29, 533–535
    See application file for complete search history.

(56) References Cited

U.S. PATENT DOCUMENTS

| | | | |
|---|---|---|---|
| 4,624,664 A * | 11/1986 | Peluso et al. .................. 604/256 |
| 4,731,061 A | 3/1988 | Matkovich |
| 4,745,950 A | 5/1988 | Mathieu |
| 4,878,516 A | 11/1989 | Mathieu |
| 4,895,570 A | 1/1990 | Larkin |
| 5,057,093 A | 10/1991 | Clegg et al. |
| 5,782,808 A | 7/1998 | Folden |
| 2012/0110951 A1* | 5/2012 | Van Groningen et al. ...... 53/425 |
| 2013/0131583 A1 | 5/2013 | Chapman et al. |

FOREIGN PATENT DOCUMENTS

CN        203525056 U      4/2014

* cited by examiner

*Primary Examiner* — Nicholas Lucchesi
*Assistant Examiner* — Melissa A Snyder
(74) *Attorney, Agent, or Firm* — Richard C. Litman

(57) ABSTRACT

The peritoneal dialysis catheter includes a thin, flexible tube, a catheter connector at a distal end of the tube, and a cylindrical cover surrounding at least a portion of the catheter connector. The catheter connector includes a tip that is configured to attach to a dialysis tubing assembly. The tip can include an externally threaded surface. A peripheral wall of the cover can surround or shield the externally threaded surface of the tip. The peritoneal dialysis catheter can include a cap, which can be removably attached to the tip.

11 Claims, 6 Drawing Sheets

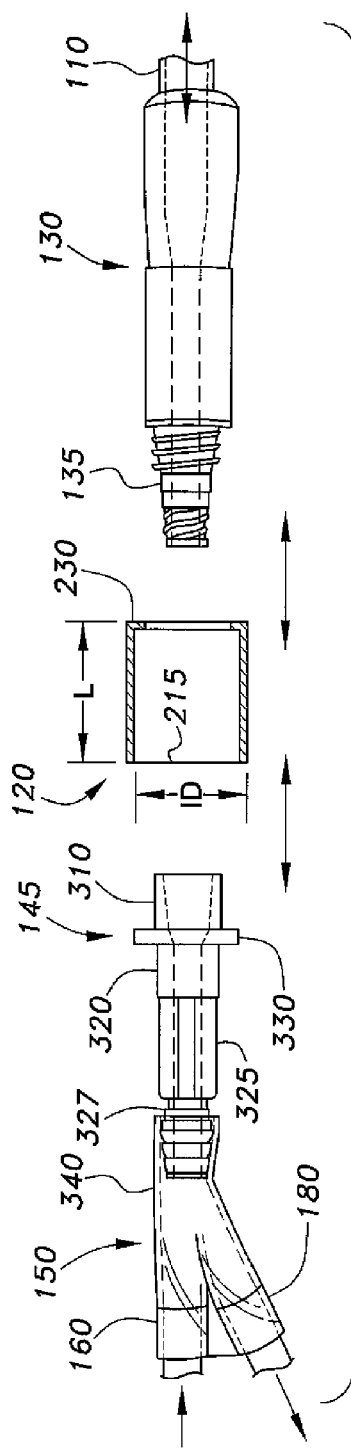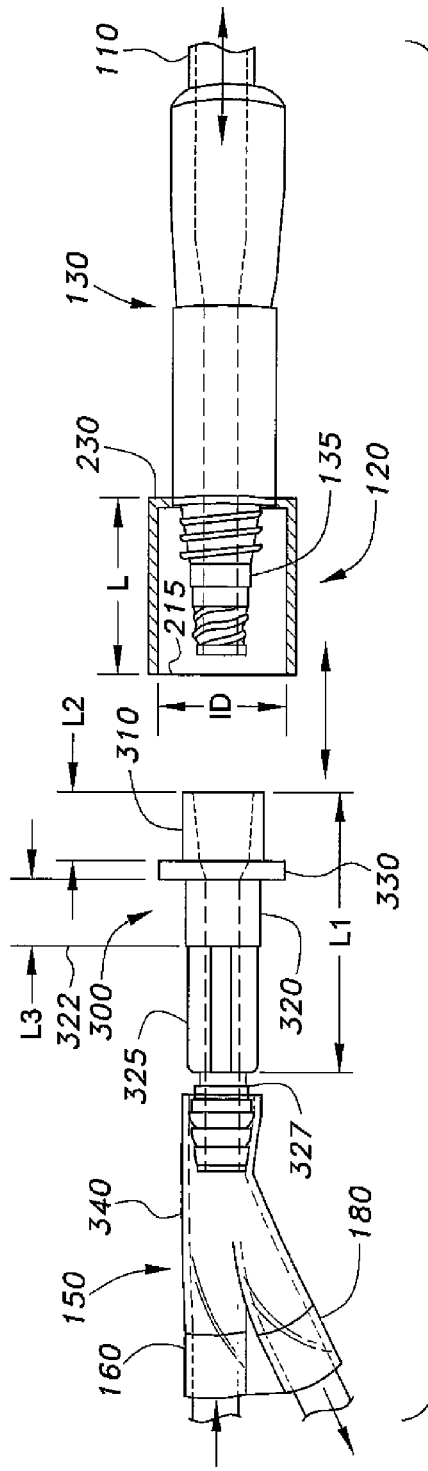
Fig. 3A
Fig. 3B

PERITONEAL DIALYSIS CATHETER

BACKGROUND OF THE INVENTION

1. Field of the Invention

The present invention generally relates to infection mitigation in medical procedures and, more specifically, to a catheter for minimizing the risk of infection during peritoneal dialysis procedures.

2. Description of the Related Art

Normally the kidneys function to filter nitrogenous waste materials and toxins from the blood to the urine. In persons with chronic renal disease the kidneys are no longer able to perform this function effectively. For many years the only form of treatment available was a hemodialysis procedure in which the patient was connected to dialysis machine which would pump out the patient's blood, filter the waste material through a semipermeable membrane, and pump the blood back into the patient. The procedure was long, tedious, time consuming, and very restrictive towards the patient's lifestyle.

In recent years, an alternative form of treatment known as peritoneal dialysis has been gaining in popularity. In peritoneal dialysis a dialysis fluid known as dialysate is inserted in the peritoneal space in the abdominal cavity. The peritoneum is a membrane comprising a visceral layer and a parietal layer, and acts as a semipermeable membrane to filter nitrogenous wastes into the dialysate. Peritoneal dialysis requires surgical implantation of a catheter apparatus through the abdominal wall, leaving a four inch catheter and eight to ten inch transfer tube depending from the exterior of the abdomen.

Peritoneal dialysis is advantageous for many patients in freeing the patient from dependence on frequent trips to hospitals and dialysis centers, and in permitting the patient to engage in normal work activities while undergoing dialysis. However, patients undergoing peritoneal dialysis can be at risk of peritonitis, a bacterial or fungal infection of the peritoneum. Left untreated, peritonitis can lead to severe, potentially life-threatening infection throughout the body. Typically, the principal entry point for pathogens into the peritoneal cavity is the catheter tip. The catheter tip can become contaminated, for example, during the process of connecting the catheter with the dialysis tubing. Contamination of the catheter can lead to passage of contaminants and microorganisms to the peritoneal cavity.

Thus, a peritoneal dialysis catheter addressing the aforementioned problems is desired.

SUMMARY OF THE INVENTION

The peritoneal dialysis catheter includes a thin, flexible tube, a catheter connector at a distal end of the tube, and a cylindrical cover surrounding at least a portion of the catheter connector. The catheter connector includes a tip that is configured to attach to a dialysis tubing assembly. The tip can include an externally threaded surface. A peripheral wall of the cover can surround or shield the externally threaded surface of the tip. The peritoneal dialysis catheter can include a cap, which can be removably attached to the tip.

These and other features of the present invention will become readily apparent upon further review of the following specification and drawings.

BRIEF DESCRIPTION OF THE DRAWINGS

FIG. 3A is a side view of the catheter connector, the cover, and an intermediary member coupled to the connector, according to the present invention.

FIG. 3B is a side view of the catheter connector with attached cover and an intermediary member, according to the present invention.

Unless otherwise indicated, similar reference characters denote corresponding features consistently throughout the attached drawings.

DETAILED DESCRIPTION OF THE PREFERRED EMBODIMENTS

Figure 1:
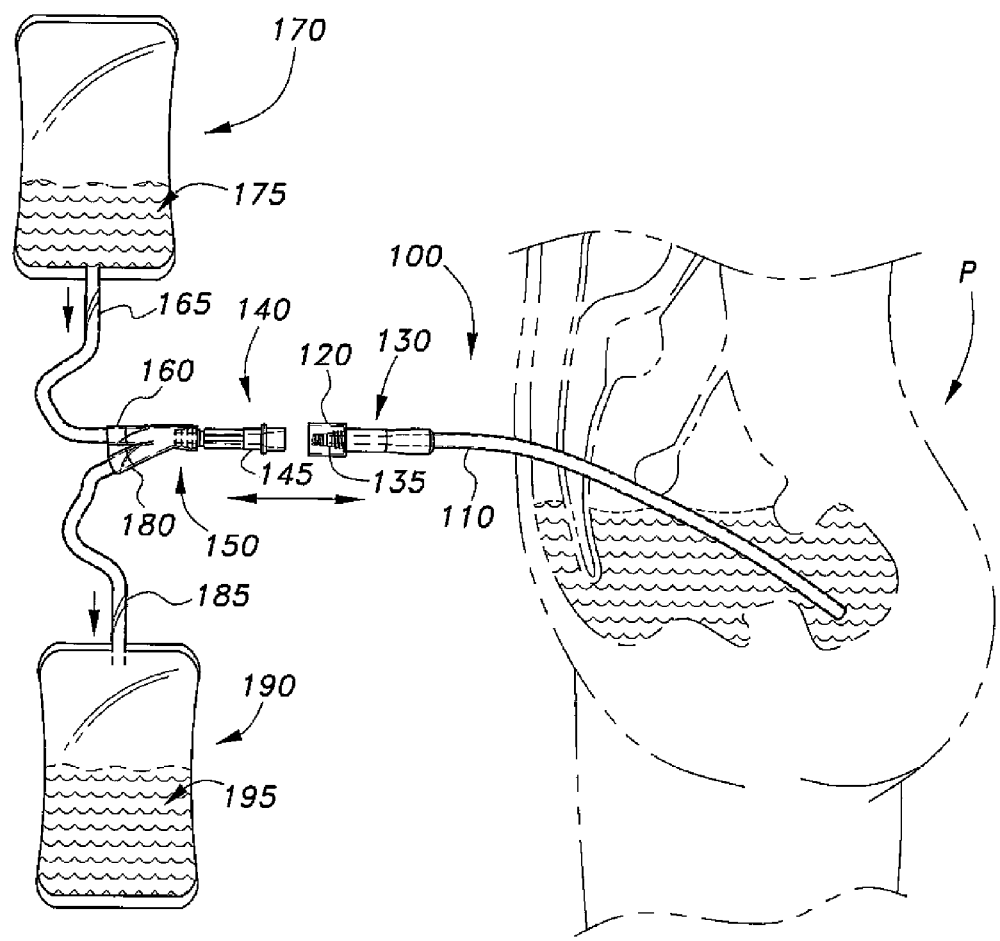
FIG. 1 is an environmental, side view of a peritoneal dialysis catheter, according to the present invention.
Figure 2:
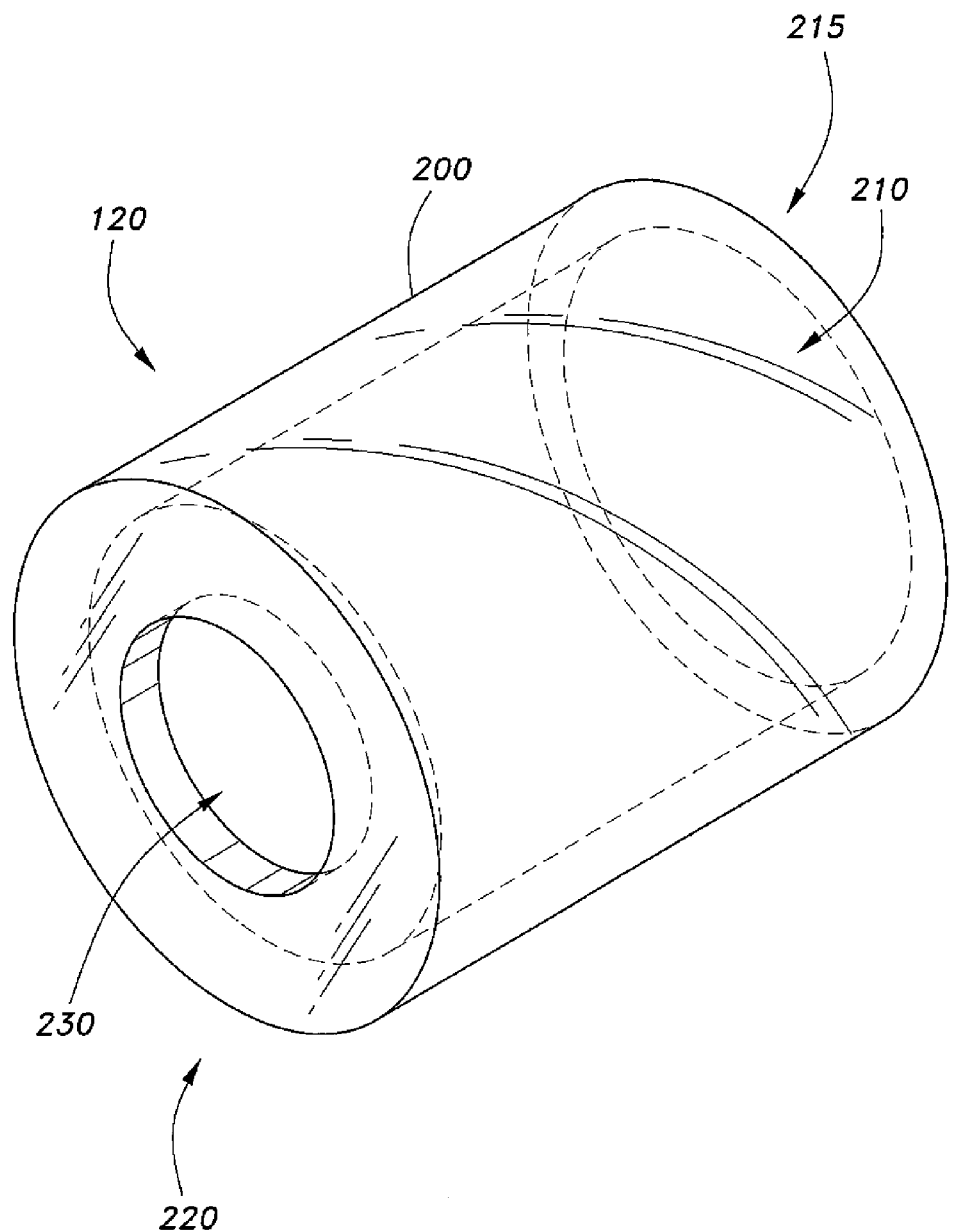
FIG. 2 is a rear, perspective view of a cover, according to the present invention.

Referring to FIGS. 1-5, an embodiment of a peritoneal dialysis catheter 100 is shown. The peritoneal dialysis catheter 100 can include a thin, flexible tube 110, a catheter connector 130 at a distal end of the tube 110, and a cover 120 surrounding at least a portion of the catheter connector 130. The catheter connector 130 can include a substantially rigid cylindrical body and a tip 135 extending from a free end of the catheter connector 130. For example, the cylindrical body of the catheter connector 130 can be substantially more rigid than the tube 11 and can have a diameter that is greater than the diameter of the tube 110. The tip 135 can be configured to attach to a dialysis tubing assembly 140. The tip 135 can be generally frusto-conical. The tip 135 can include an externally threaded surface, e.g., helical ridges or threaded portions disposed on an outer surface of the tip 135, to facilitate attachment to the dialysis tubing assembly 140, as discussed in detail below. The cover 120 can be affixed to the cylindrical body of the catheter connector 130, spaced from the tip 135. For example, one end of the cover 120 can be affixed to the cylindrical body of the catheter connector 130, such that a peripheral wall of the cover 120 surrounds or shields the externally threaded surface of the tip 135. The catheter 100 can include a cap 400 (FIGS. 4 and 5), which can be removably attached to the tip 135. For example, the cap 400 can be a screw cap with interior threaded portions for mating with the exterior threaded portions of the tip 135. The cap 400 can be positioned within the peripheral wall of the cover 120 and over the tip 135.

The peritoneal dialysis catheter 100 can be surgically implanted in the abdominal wall of a patient, such that a proximal end of the peritoneal dialysis catheter 100 extends into the peritoneal cavity, while an opposing distal end of the peritoneal dialysis catheter 100 remains outside of the patient's body. The catheter 100 can exit the abdomen about 4 inches laterally from and 1 inch inferior to the umbilicus. When draining or instilling fluid from or to the peritoneal space, the cap 400 can be removed from the catheter 100 and the tip 135 of the catheter 100 can be connected to the one or more disposable containers 170 and 190 by the dialysis tubing assembly 140. The cover 120 can protect the tip 135 from contamination during this process. When not replacing fluid, the cap 400 can be left in place on the tip 135 of the catheter 100.

The dialysis tubing assembly 140 can include an intermediary member 145, a tubing connector 150, and dialysate tubes 165 and 185. The intermediary member 145 can have a first section 310, a second section 320, a third section 325, a fourth section 327, and a lumen extending therethrough. The first and second sections 310, 320 of the intermediary member 145 can together form an inner frusto-conical cavity with threaded portions for mating with the externally threaded portions of the tip 135. The third section 325 of the intermediary member 145 can be manipulated by a user to twist the intermediary member 145 in an appropriate direction for attachment to or detachment from the tip 135 of the catheter connector 130. The fourth section 327 of the intermediary member 145 can be inserted into a stem portion 340 of the tubing connector 150. The tubing connector 150 can have a generally Y-shape, including a first leg 160 coupled the first tube 165 and a second leg 180 coupled to the second tube 185. The tubing connector 150 can be connected to dialysate tubes 165, 185, in communication with the one or more containers, 170 and 190, respectively.

Figure 3C:
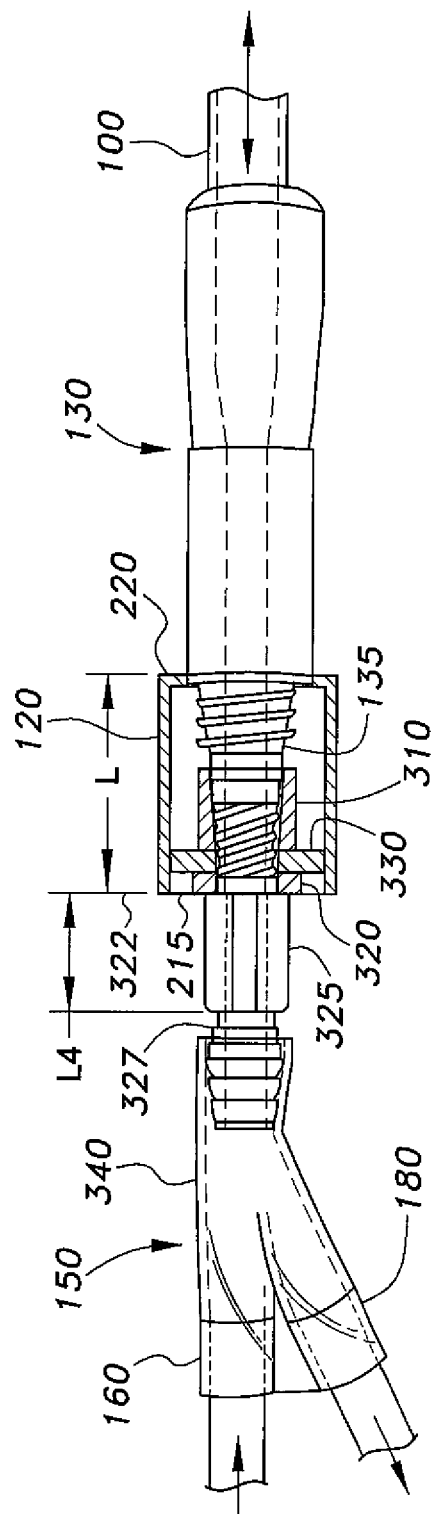
FIG. 3C is a side view of the catheter connector with attached cover and an intermediary member coupled to the catheter connector, according to the present invention.

The cover 120 includes a cylindrical body 200 with a first end 210 having a first opening 215 and a second end 220 having a second opening 230. The first end 210 can receive the intermediary member 145 of the dialysis tubing 140 and the second end 220 can receive the tip 110 of the catheter connector 130. Once the catheter 100 is connected to the intermediary member 145, the cover 120 can surround the tip 135 of the catheter connector 130 and the first and second sections 310, 320 of the intermediary member 145, as illustrated in FIG. 3C. An end portion 322 of the second section 320 of the intermediary member 140 can be substantially even with the first end 210 of the cover 120, as illustrated in FIGS. 3B and 3C, to prevent contaminants from coming in contact with the tip 135 of the catheter connector 130.

In addition to the components described herein, the peritoneal dialysis catheter 100 can include components of peritoneal dialysis catheters commonly used at present. Further, the cover 120, the catheter connector 130, the tube 110, the intermediary member 145, and the tubing connector 150 can be made from any suitable medical grade material, such as plastic. Examples of suitable plastics include polyethylene, polypropylene, polystyrene, polyester, polycarbonate, and polyvinyl chloride. Preferably, the cover 120 is made from a transparent material, such as a transparent, plastic material. The cover 120, can be of any suitable size. Preferably, the cover has a length (L) of about 2.5 cm and an interior diameter (ID) of about 2 cm.

The intermediary member 145 can have any suitable dimension. Preferably, the intermediary member 145 has a length (L1) of about 3.3 cm, so as to securely retain the tip 135 of the catheter connector 130. The first section 310 of the intermediary member 145 can have a length (L2) of about 1.5 cm, the second section 320 of the intermediary member 145 can have a length L3 of about 0.8 cm, the third section 325 of the intermediary member 145 can have a length L4 of about 1 cm, and the fourth section 327 of the intermediary member 145 can have any length suitable to secure the intermediary member 145 to the tubing connector 150. The intermediary member 145 can include a flange 330 having a substantially circular shape, which can abut the interior wall of the cover, so as to create a substantially tight fit inside the cover 120, as illustrated in FIG. 3C.

Figure 4:
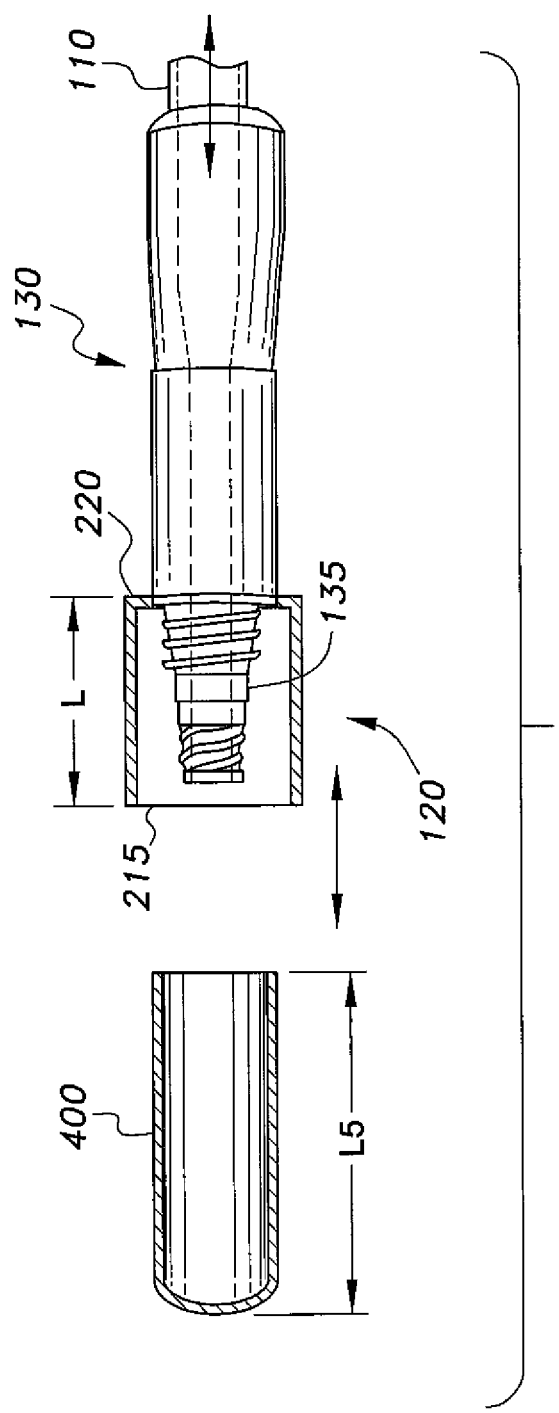
FIG. 4 is a side view of the catheter connector and the cap, according to the present invention.
Figure 5:
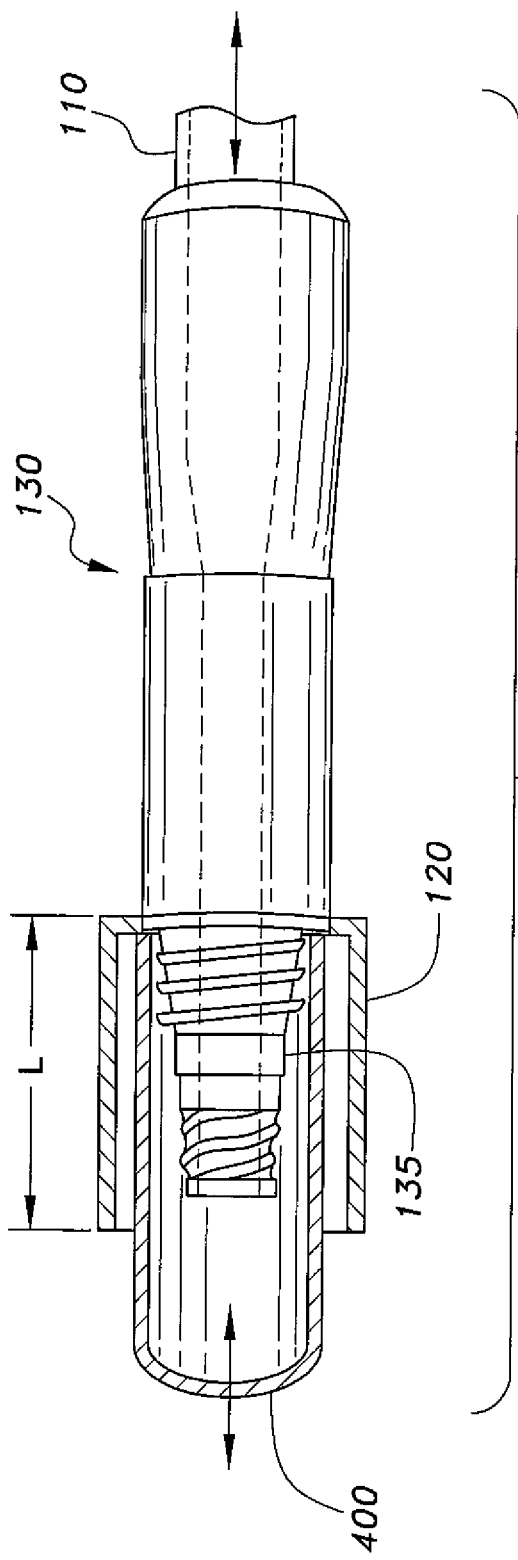
FIG. 5 is a side view of the catheter connector and the cap affixed to the tip, according to the present invention.

A kit for peritoneal dialysis can include the tube 110, the catheter connector 130, the cover 120, the intermediary member 145, and the cap 400, such as a cylindrical screw cap, as illustrated in FIGS. 4 and 5. The cap 400 can be made from any suitable medical grade material, such as plastic, such as polyethylene, polypropylene, polystyrene, polyester, polycarbonate, and polyvinyl chloride. The cap 400 can be configured to protrude beyond the cover 120 once positioned on the tip 135, to facilitate application and removal of the cap 400. The cap 400 can have a length (L5) of about 3.5 cm. The cap 400 can be configured to substantially prevent the tip 135 of the catheter connector 130 from coming in contact with any surrounding materials and, thereby, minimize the risk of infection.

After peritoneal dialysis is completed, the third section 325 of the intermediary member 145 can be manipulated to loosen the intermediary member 145 from the tip 135 of the catheter connector 130, e.g., by twisting in a suitable direction, such as a counter-clockwise direction. The cover 120 shields the tip 135 from contamination during this process. Once the intermediary member 145 is disconnected from the tip 135 of the catheter connector 130, the cap 400 can be used to cover the tip 135 of the catheter connector 130, as illustrated in FIG. 5, so as to prevent the tip 135 of the catheter connector 130 from coming in contact with any surrounding materials and, thereby, minimizing the risk of contamination.

It is to be understood that the present invention is not limited to the embodiments described above, but encompasses any and all embodiments within the scope of the following claims.

I claim:

1. A peritoneal dialysis catheter comprising:
    a flexible tube having a distal end and an opposing, proximal end;
    a catheter connector at the distal end of the flexible tube, the catheter connector including a cylindrical body and a connection tip at a free end of the cylindrical body, the connection tip including an exterior surface with threaded portions and a terminating distal end; and
    a cover affixed to the cylindrical body, the cover surrounding the exterior threaded surface of the connection tip, and extends beyond the terminating distal end of the connection tip;
    wherein the connection tip is substantially enclosed within the interior of the cover.

2. The peritoneal dialysis catheter according to claim 1, wherein the catheter connector has a diameter larger than a diameter of the flexible tube.

3. The peritoneal dialysis catheter according to claim 1, wherein the tip is frusto-conical.

4. The peritoneal dialysis catheter cover according to claim 1, wherein the cover has a length of about 2.5 cm and a diameter of about 2 cm.

5. The peritoneal dialysis catheter according to claim 1, wherein the cover is transparent;
    wherein the connector tip end is visible therethrough.

6. The peritoneal dialysis catheter according to claim 1, further comprising a cap, the cap including interior threaded portions for mating with the exterior threaded portions of the tip.

7. The peritoneal dialysis catheter according to claim 6, wherein the cover has a length of about 2.5 cm and a diameter of about 2 cm, and the cap has a length of about 3.5 cm.

8. A kit for peritoneal dialysis comprising:
    a flexible tube having a distal end and an opposing, proximal end a catheter connector at a distal end of the flexible tube, the catheter connector including a cylindrical body, a threaded connection tip at a free end of the cylindrical body having a terminating distal end, and a cover affixed to the cylindrical body and surrounding the threaded connection tip;
    wherein the cover extends beyond the terminating distal end of the connection tip so as to substantially enclose the connection tip within the interior of the cover;

an intermediary member having a first section, a second section, a third section, a fourth section, and a lumen extending therethrough, the first and second sections of the intermediary member together forming an inner cavity with threaded portions for receiving and engaging the tip; and a cap having an inner cavity with threaded portions for receiving and engaging the connection tip.

9. The kit for peritoneal dialysis according to claim 8, wherein the cover is transparent.

10. The kit for peritoneal dialysis according to claim 8, wherein the cover has a length of about 2.5 cm and an internal diameter of about 2 cm.

11. A catheter for use in peritoneal dialysis treatment, the catheter comprising:

a flexible tube having a distal end and an opposing, proximal end;

a catheter connector at the distal end of the flexible tube, wherein the catheter connector has a diameter larger than a diameter of the flexible tube;

the catheter connector consisting of:

a cylindrical body; and a frusto-conical connection tip at a free end of the cylindrical body, the connection tip including an exterior surface with a threading, and a terminating distal end;

a transparent cover affixed to the cylindrical body, the cover surrounding the threading of the exterior surface of the connection tip, and extending beyond the terminating distal end of the connection tip;

wherein the connection tip is substantially enclosed within the interior of the cover;

wherein the connector tip end is visible therethrough; and wherein the cover has a length of about 2.5 cm and a diameter of about 2 cm; and a removable cap, the removable cap having an interior threading for mating with the exterior threaded portions of the connection tip;

wherein the removable cap has a length of about 3.5 cm.

* * * * *